(12) United States Patent
Wu

(10) Patent No.: US 11,090,257 B2
(45) Date of Patent: Aug. 17, 2021

(54) HUMAN BODY CLEANER AND MANUFACTURING METHOD THEREOF

(71) Applicant: Shu-Chun Wu, Kaohsiung (TW)

(72) Inventor: Shu-Chun Wu, Kaohsiung (TW)

( * ) Notice: Subject to any disclaimer, the term of this patent is extended or adjusted under 35 U.S.C. 154(b) by 279 days.

(21) Appl. No.: 16/095,167

(22) PCT Filed: Jun. 14, 2016

(86) PCT No.: PCT/CN2016/085677
§ 371 (c)(1),
(2) Date: Oct. 19, 2018

(87) PCT Pub. No.: WO2017/197688
PCT Pub. Date: Nov. 23, 2017

(65) Prior Publication Data
US 2019/0142732 A1 May 16, 2019

(30) Foreign Application Priority Data
May 20, 2016 (CN) .......................... 201610337991.1

(51) Int. Cl.
*A61K 8/97* (2017.01)
*A61Q 5/02* (2006.01)
*A61Q 19/10* (2006.01)
*A61K 8/9794* (2017.01)
*A61Q 5/00* (2006.01)
*A61Q 19/00* (2006.01)

(52) U.S. Cl.
CPC .............. *A61K 8/97* (2013.01); *A61K 8/9794* (2017.08); *A61Q 5/006* (2013.01); *A61Q 5/02* (2013.01); *A61Q 19/10* (2013.01); *A61Q 19/007* (2013.01)

(58) Field of Classification Search
CPC ......... A61K 8/97; A61K 8/9794; A61P 17/00; A61P 31/10; A61Q 19/007; A61Q 19/10; A61Q 5/006; A61Q 5/02
See application file for complete search history.

(56) References Cited

FOREIGN PATENT DOCUMENTS

| CN | 102885959 A | 1/2013 |
|---|---|---|
| CN | 103505388 A | 1/2014 |
| GB | 842404 A | 7/1960 |
| GB | 2182943 A | 5/1987 |
| JP | 2015-65928 A | 4/2015 |

OTHER PUBLICATIONS

Reid, K. et al "Garlc and Organosulfur Compounds" Linus Pauling Institute, Micronutrient Information Center, Oregon State University, retreived online Apr. 2021 <https://lpi.oregonstate.edu/mic/food-beverages/garlic>, archived Dec. 2016, 30 pp. (Year: 2021).*
International Search Report in corresponding International Application No. PCT/CN2016/085677, dated Feb. 22, 2017.

* cited by examiner

*Primary Examiner* — Aaron J Kosar
(74) *Attorney, Agent, or Firm* — Bacon & Thomas, PLLC

(57) ABSTRACT

The present invention discloses a human body cleaner and manufacturing method thereof. The human body cleaner comprises 1% wt~60% wt of garlic extract, and 40% wt~99% wt of cleaning agent. The method for manufacturing the human body cleaner comprises the following steps: preparing a plurality of garlics, adding water in a predetermined ratio to a plurality of garlics to obtain a garlic mixture, adding yeast in a predetermined ratio to the garlic mixture and leaving it to stand for a period of time for fermentation to obtain a garlic fermentation broth, performing cryogenic distillation on the garlic fermentation broth to obtain a garlic extract, and adding a cleaning agent in a predetermined ratio to the garlic extract for mixture to obtain the human body cleaner. The present invention uses the herbal human body cleaner made from garlic to clean human body and reduce symptoms of dandruff. Moreover, long-term use of the present invention will not cause either antibiotic resistance or environmental degradation.

7 Claims, 2 Drawing Sheets

HUMAN BODY CLEANER AND MANUFACTURING METHOD THEREOF

BACKGROUND OF THE INVENTION

1. Field of the Invention

The present invention relates to a manufacturing method, particularly to a human body cleaner and manufacturing method thereof.

2. Description of the Prior Art

In addition to keeping warm and protecting scalp, hair also can make people attractive. However, dandruff is an annoying problem, although it is not harmful to health, it is accompanied by symptoms like itchy scalp, increased head off dander which often results in social communication disorder.

Contact dermatitis and fungal infections resulting from seborrheic dermatitis, psoriasis, shampoo, hair dye, styling products and other chemicals are general causes of dandruff. Besides, a fast paced life let people have symptoms like stress, emotional tension, malnutrition, lack of sleep and fatigue, which also accelerate the formation of dandruff.

Seborrheic dermatitis is the main cause of dandruff, which is relevant to the proliferation of *Malassezia furfur* on the skin. These fungi metabolize triglycerides in the sebum to form oleic acid, when oleic acid filters into the stratum corneum of the epidermis, it will irritate sensitive skins and interfere physiological constancy of keratinocytes, which leads to abnormal shedding reaction to cause dandruff.

The ingredients of current anti-dandruff shampoo include ketoconazole, zinc pyrithione (ZP), salicylic acid, selenium sulfide (SeS2), ciclopiroxolamine (CPO), piroctoneolamine, pyridinethione salts and active climbazole, so that it has antibacterial, anti-dandruff effect and can relieve itching. However, these antidandruff agents in current anti-dandruff shampoo are made from chemical synthesis, which will cause antibiotic resistance, and the dose will be increased at certain intervals, or the therapeutic effect will be reduced, furthermore, it will affect the environment and health. Therefore, more and more people are seeking natural shampoo.

Take garlic for example, it has a strong bactericidal effect to inhibit or even kill a variety of bacteria and viruses, so it is widely used on the skin disease like eczema, athlete's foot, and diaper rash, but it is rarely used for cleaning human body or treating dandruff.

In recent years, the garlic price in Taiwan fluctuates widely, following the market mechanism, farmers have no choice but to accept dissatisfied offers, low prices and losses. If farmers do not follow the market mechanism, they have to process garlic at their own expense, or abandon rotten garlic, which increases food waste and cost.

If garlic can be applied on the human body cleanser or shampoo, it cannot only solve overproduction problem, but also can create added value of garlic, so that farmers' income can be increased. For the cleaning product manufacturers, they can provide consumers with affordable and safer natural cleaning products. Therefore, consumers will have willingness to use it, which enhances competitiveness in the market.

Therefore, the present invention is to solve the problem that the antidandruff agent in current anti-dandruff shampoo are made from chemical synthesis, which will cause antibiotic resistance, and the dose has to be increased at certain intervals, or the therapeutic effect will be reduced, furthermore, it will affect the environment and health.

SUMMARY OF THE INVENTION

Therefore, an objective of an embodiment of the present invention is to provide a human body cleaner, comprising 1% wt~60% wt of garlic extract, and 40% wt~99% wt of cleaning agent.

Another technique of an embodiment of the present invention is that the cleaning agent further includes 10% wt~20% wt of surfactant, 10% wt~25% wt of purified water, and 5% wt~15% wt of nutrient solution.

Another technique of an embodiment of the present invention is that the surfactant used for removing grease and adhesive is selected from a set consisting sodium dodecyl sulfate, sodium lauryl ether sulfate, sodium cocoamphoacetate, or coconut monoethanolamide and combinations thereof, and the nutrient solution is selected from a set consisting collagen, fibroin, vitamins and combinations thereof.

Therefore, another objective of an embodiment of the present invention is to provide a method for manufacturing the human body cleaner, comprising the following steps.

Firstly, a plurality of garlics are prepared. Water in a predetermined ratio is added to a plurality of garlics to obtain a garlic mixture. Then, yeast in a predetermined ratio is added to the garlic mixture, which is left to stand for fermentation to obtain a garlic fermentation broth. Then, cryogenic distillation is performed on the garlic fermentation broth to obtain a garlic extract. Lastly, a cleaning agent in a predetermined ratio is added to the garlic extract for mixture to obtain the human body cleaner.

Another technique of an embodiment of the present invention is that an additive is added to the garlic mixture and the additive is selected from a set consisting tea leaf, citrus peel, *chrysanthemum* and combinations thereof. Furthermore, the purified water and nutrient solution in a predetermined ratio are added to the garlic extract for mixture.

Another technique of an embodiment of the present invention is that the ratio of plural garlics to water is 5:1, and the ratio of the garlic mixture to the yeast is 1000:1.

Another technique of an embodiment of the present invention is that an accelerator is added to the garlic fermentation broth, and the accelerator is composed of carbohydrate.

Another technique of an embodiment of the present invention is that 30%~70% of the garlic fermentation broth's top layer is extracted, and the fermentation period of the garlic mixture is 3 months. The cleansing agent includes surfactant, purified water and nutrient solution.

Another technique of an embodiment of the present invention is that a plurality of garlics are placed at a predetermined temperature for 30 days.

Another technique of an embodiment of the present invention is that preliminary distillation is performed on the garlic mixture at 100~200° C., and cryogenic distillation is performed on the garlic fermentation broth at 200~400° C. to obtain a garlic extract.

An advantage of an embodiment of the invention is that the processed garlic used as human body cleaner can solve the garlic overproduction problem, and it can increase added value of garlic to improve the farmer's income, developing the intense agriculture. Furthermore, the herbal human body cleaner made from garlic can clean human body and reduce symptoms of dandruff. Moreover, long-term use of the present invention will not cause either antibiotic resistance or environmental degradation. Therefore, it is distinguished from current cleaning products, and has competition in current market.

DETAILED DESCRIPTION OF THE PREFERRED EMBODIMENTS

Figure 1:
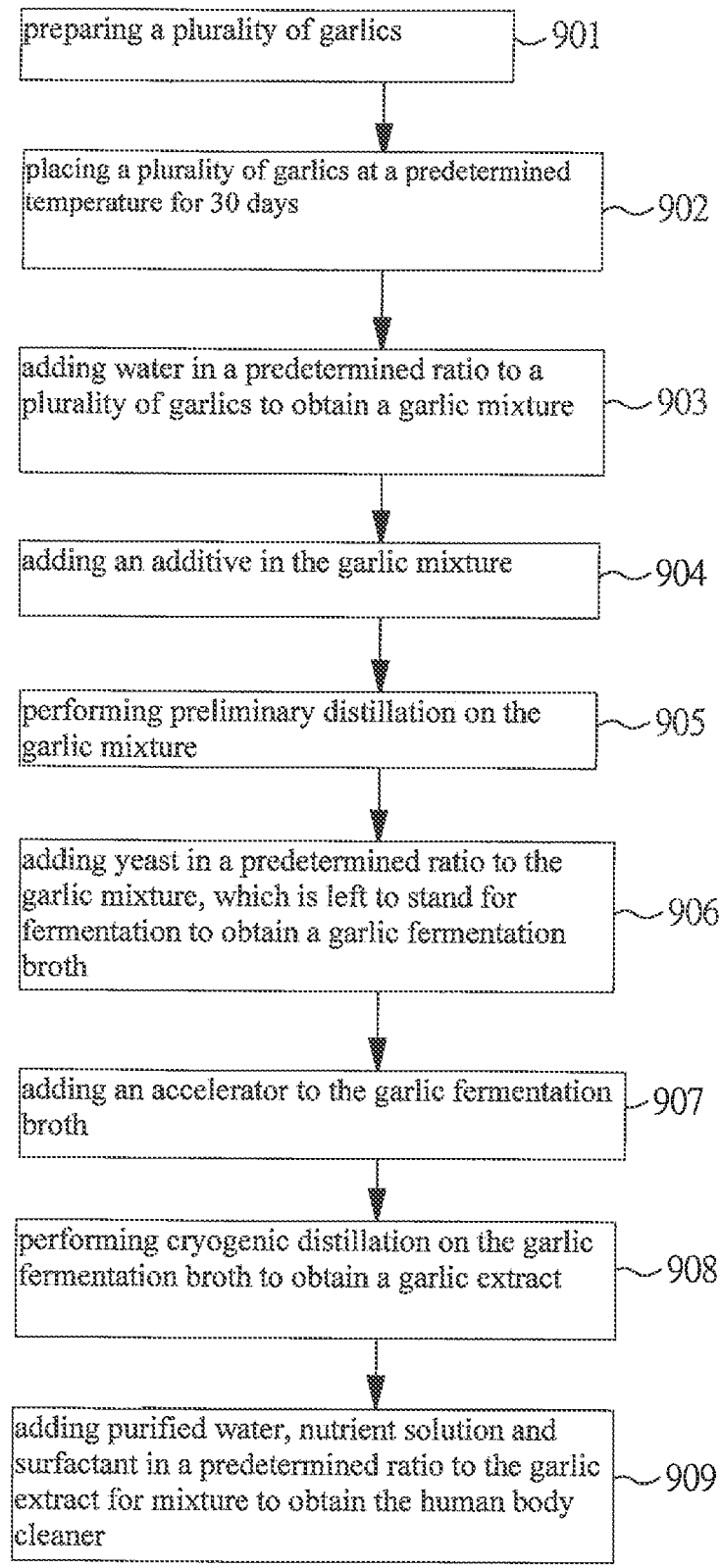
FIG. 1 is a flow chart of a preferred embodiment according to the method for manufacturing the human body cleaner.

Specific structural and functional details disclosed herein will become apparent from the following description of the preferred embodiment of the present invention taken in conjunction with the accompanying drawings, which provides better understanding to a person having ordinary skill in the art but shall not be construed as limiting the invention.

More specifically, the human body cleaner 8 is used for shampoo in the preferred embodiment, while in practice, the human body cleaner 8 also can be used for body wash, facial cleanser and so on, and shall not be construed as limiting the invention.

The human body cleaner 8 comprises 1% wt~60% wt of garlic extract 7, and 40% wt~99% wt of cleaning agent. The cleaning agent is composed of 10% wt~25% wt of purified water 36, 5% wt~15% wt of nutrient solution 37, and 10% wt~20% wt of surfactant 38.

The nutrient solution 37 is selected from a set consisting collagen, fibroin, vitamins and combinations thereof, so it can provide nutrition to hair to avoid easy breaking during hair cleaning.

Besides, the surfactant 38 used for removing grease and adhesive is selected from a set consisting sodium dodecyl sulfate, sodium lauryl ether sulfate, sodium cocoamphoacetate, or coconut monoethanolamide and combinations thereof. In practice, different surfactants 38 can be mixed to obtain appropriate cleaning and forming effect, so that the convenience of cleaning hair can be improved.

Figure 2:
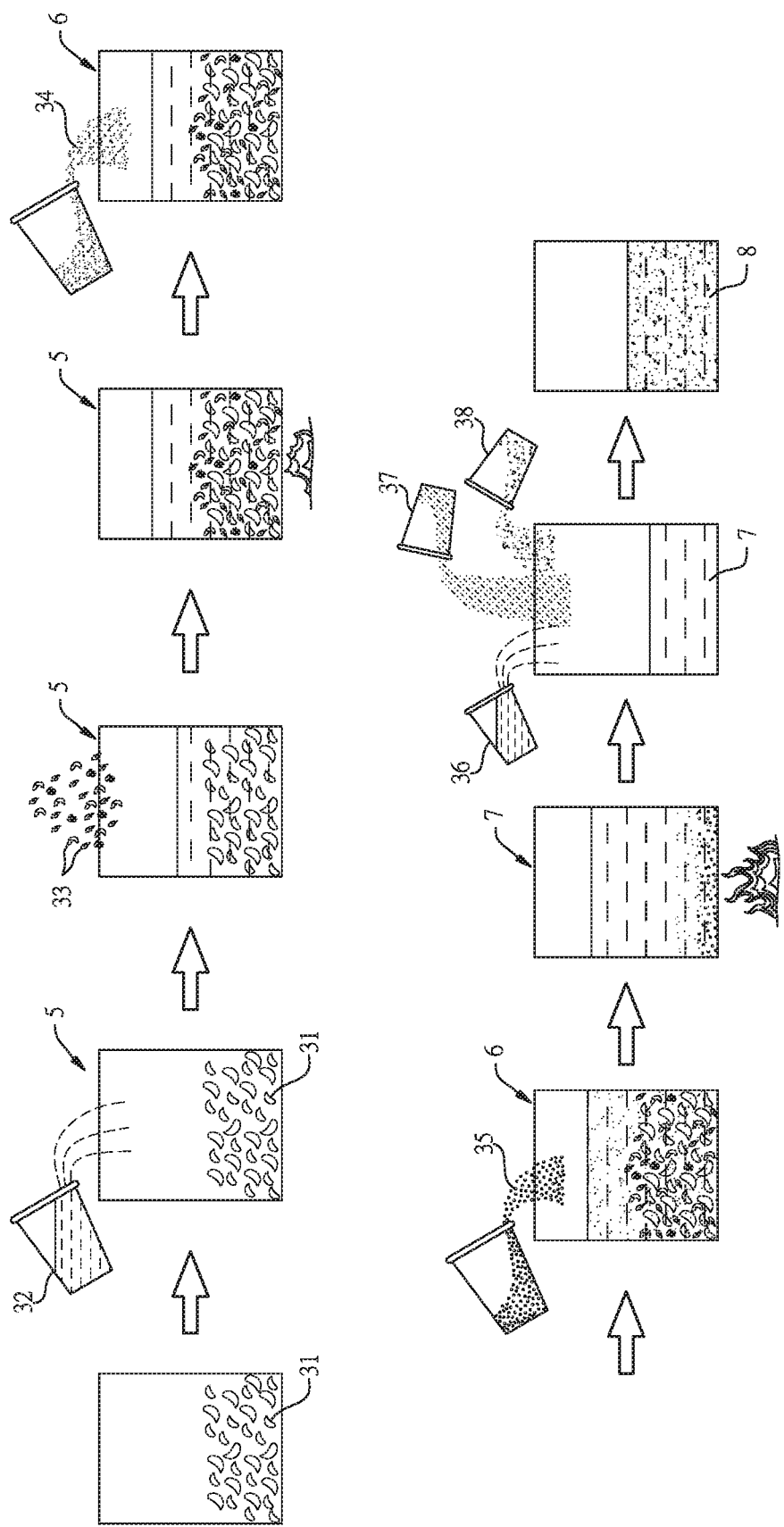
FIG. 2 is a drawing of the preferred embodiment according to the present invention.

With reference to FIGS. 1 and 2, a method for manufacturing the human body cleaner 8 is depicted, comprising the following steps.

Firstly, in step 901, a plurality of garlics 31 are prepared. In the preferred embodiment, Taiwan garlic 31 is choosen.

Because the price of agricultural products in Taiwan fluctuates widely, when overproduction occurs, agricultural products have to be sold at low price, farmers' income is unstable. Processing the garlic 31 for human body cleaner can solve the overproduction of the garlic 31, and can increase added value of the garlic 31 to improve the farmer's income, developing the intense agriculture.

In step 902, a plurality of garlics 31 are placed at a predetermined temperature for 30 days. In the preferred embodiment, a plurality of garlics 31 are placed at room temperature for 30 days.

In step 903, water 32 in a predetermined ratio is added to a plurality of garlics 31 to obtain a garlic mixture 5. Particularly, in step 902, the ratio of plural garlics 31 to water 32 is 5:1

In step 904, an additive 33 is added to the garlic mixture 5 and the additive 33 is selected from a set consisting tea leaf, citrus peel, *chrysanthemum* and combinations thereof. In practice, other natural additives 33 can also be added to, and shall not be construed as limiting the invention.

In step 905, preliminary distillation is performed on the garlic mixture 5 at 100~200° C.

The garlic mixture 5 used for preliminary distillation is extracted from 30%~70% of its top layer, so it can avoid extracting from the garlic 31 or the additive 33 at the bottom.

In step 906, yeast 34 in a predetermined ratio is added to the garlic mixture 5, which is left to stand for fermentation to obtain a garlic fermentation broth 6, and the ratio of the garlic mixture 5 to the yeast 34 is 1000:1.

In the preferred embodiment, the garlic mixture 5 is placed at room temperature for 3 months. Although fermentation can be carried out in a variety of ways, it is common technique and is not primary feature of the present invention, and so details related to this are not explained further herein.

In step 907, an accelerator 35 is added to the garlic fermentation broth 6, and the accelerator 35 is composed of carbohydrate, such as brown sugar, white sugar and rock sugar. By adding the accelerator 35 helps the yeast 34 actively ferment. Materials containing any form of sugar can be used as the accelerator 35, and shall not be construed as limiting the invention.

In step 908, cryogenic distillation is performed on the garlic fermentation broth 6 to obtain a garlic extract 7. In step 908, cryogenic distillation is performed on the garlic fermentation broth 6 at 200~400° C. to obtain the garlic extract 7. According to the inventor's experiment, the pH value of the garlic extract 7 is 3.4~3.6, which is weak acid good for sterilization and reducing inflammation.

It should be noted that the garlic fermentation broth 6 used for cryogenic distillation is extracted from 30%~70% of its top layer, so it can avoid extracting from the garlic 31 or the additive 33 at the bottom, and the purity of the garlic extract 7 can be improved.

Lastly, in step 909, adding purified water 36, nutrient solution 37 and surfactant 38 in a predetermined ratio to the garlic extract 7 for mixture. The human body cleaner 8 is composed of 1% wt~60% wt of garlic extract 7, 10% wt~25% wt of purified water 36, 5% wt~15% wt of nutrient solution 37, and 10% wt~20% wt of surfactant 38.

When the human body cleaner 8 is used for shampoo, because the garlic 31 has fast permeability and powerful sterilization, it can inhibit *Malassezia furfur* to reduce dandruff and inflammation, relieving itching. Moreover, the organosulfur compounds in the garlic 31 can control the sebum production, so that the hair will not greasy, and users with oily hair can also be satisfied. Therefore, the effects of cleaning, controlling the dandruff and protecting hair can be obtained.

With the above descriptions, following advantages can be obtained by the present invention:

1. Simple Process

Preparing a plurality of garlics 31, adding the water 32 in a predetermined ratio, the additive 33, the yeast 34 in a predetermined ratio, and the accelerator 35 for fermentation and cryogenic distillation to obtain the garlic extract 7. Then, adding purified water 36, nutrient solution 37 and surfactant 38 in a predetermined ratio to the garlic extract 7 for mixture to obtain the human body cleaner 8. During the process, methods and equipment are simplified, so the cost can be reduced quite substantially and competitiveness in the market can be increased.

2. Safety and Environment Consideration

The herbal human body cleaner 8 made from garlic 31 can reduce symptoms of dandruff, and long-term use of the present invention will not cause antibiotic resistance or be harmful to health, not mention to environmental degradation.

3. Increasing Added Value of the Garlic 31

The human body cleaner 8 made from the processed garlic 31 cannot only solve the overproduction of the garlic 31, but also can increase added value of garlic 31 to improve the farmer's income, developing the intense agriculture.

In conclusion, in the present invention, adding the water 32 in a predetermined ratio, the additive 33, the yeast 34 in a predetermined ratio, and the accelerator 35 to a plurality of garlics 31 for fermentation and cryogenic distillation to obtain the garlic extract 7. Then, adding purified water 36, nutrient solution 37 and surfactant 38 in a predetermined ratio to the garlic extract 7 for mixture to obtain the human body cleaner 8. During the process, methods and equipment are simplified, so the cost can be reduced quite substantially. The herbal human body cleaner 8 made from garlic 31 can reduce symptoms of dandruff, and long-term use of the present invention will not cause antibiotic resistance or be harmful to health, not mention to environmental degradation. Therefore, it is distinguished from current cleaning products, and has competition in current market.

The foregoing embodiment is merely in relation to a preferred embodiment and shall not be construed as limiting the invention. It is to be understood that many other possible modifications and variations can be made without departing from the spirit and scope of the invention as hereinafter claimed. The scope of the present invention shall be construed by claims.

What is claimed is:

1. A method for manufacturing a human body cleaner, comprising the following steps:
    (a) preparing a plurality of garlics;
    (b) adding water in a predetermined ratio to the plurality of garlics to obtain a garlic mixture;
    (c) adding yeast in a predetermined ratio to the garlic mixture, which is left to stand for fermentation to obtain a garlic fermentation broth;
    (d) performing cryogenic distillation on the garlic fermentation broth to obtain a garlic extract; and
    (e) adding a cleaning agent in a predetermined ratio to the garlic extract for mixture to obtain the human body cleaner.

2. The method for manufacturing the human body cleaner as claimed in claim 1, further comprising a step (f) disposed between step (b) and step (c), in step (f) adding an additive in the garlic mixture, the additive being selected from a set consisting of tea leaf, citrus peel, *chrysanthemum* and combinations thereof; and in step (e) adding purified water and nutrient solution in a predetermined ratio to the garlic extract for mixture.

3. The method for manufacturing the human body cleaner as claimed in claim 2, wherein in step (b) the ratio of plural garlics to water is 5:1; and in step (c) the ratio of the garlic mixture to the yeast is 1000:1.

4. The method for manufacturing the human body cleaner as claimed in claim 3, further comprising a step (g) disposed between step (c) and step (d), and in step (g) adding an accelerator to the garlic fermentation broth, and wherein the accelerator is composed of carbohydrate.

5. The method for manufacturing the human body cleaner as claimed in claim 4, wherein: in step (c) the fermentation period of the garlic mixture is 3 months; step (d) comprises extracting 30% to 70% of the garlic fermentation broth's top layer; and in step (e), the cleansing agent being made from surfactant, purified water, and nutrient solution.

6. The method for manufacturing the human body cleaner as claimed in claim 5, further comprising a step (h) disposed between step (a) and step (b), and in step (h) a plurality of garlics being placed at a predetermined temperature for 30 days.

7. The method for manufacturing the human body cleaner as claimed in claim 6, further comprising a step (i) disposed between step (f) and step (c), in step (i) performing preliminary distillation on the garlic mixture at 100° C. to 200° C.; and in step (d) performing cryogenic distillation on the garlic fermentation broth at 200° C. to 400° C. to obtain a garlic extract.

* * * * *